(12) United States Patent
Hu et al.

(10) Patent No.: US 11,037,656 B2
(45) Date of Patent: Jun. 15, 2021

(54) DATA-DRIVEN PREDICTION OF DRUG COMBINATIONS THAT MITIGATE ADVERSE DRUG REACTIONS

(71) Applicant: INTERNATIONAL BUSINESS MACHINES CORPORATION, Armonk, NY (US)

(72) Inventors: Jianying Hu, Bronx, NY (US); Ying Li, Fort Lee, NJ (US); Zhaonan Sun, Elmsford, NY (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/654,539

(22) Filed: Oct. 16, 2019

(65) Prior Publication Data

US 2020/0051670 A1 Feb. 13, 2020

Related U.S. Application Data

(63) Continuation of application No. 15/257,535, filed on Sep. 6, 2016, now Pat. No. 10,490,301.

(51) Int. Cl.
*G06N 5/02* (2006.01)
*G16C 20/30* (2019.01)
*G06N 5/00* (2006.01)

(52) U.S. Cl.
CPC .............. *G16C 20/30* (2019.02); *G06N 5/00* (2013.01); *G06N 5/022* (2013.01)

(58) Field of Classification Search
None
See application file for complete search history.

(56) References Cited

PUBLICATIONS

A. Abadie, "Semiparametric Difference-in-Differences Estimators"; The Review of Economic Studies, 2005, Issue 72, pp. 1-19.
A. S. Alanazi, "Systematic Review and Meta-analysis of Efficacy and Safety of Combinational Therapy with Metformin and Dipeptidyl Peptidase-4 Inhibitors", Saudi Pharmaceutical Journal, Nov. 2015, vol. 23, No. 6, pp. 603-613.
(Continued)

*Primary Examiner* — Hal Schnee
(74) *Attorney, Agent, or Firm* — Kristofer L. Haggerty

(57) ABSTRACT

Predicting beneficial drug combinations mitigating adverse drug reactions identifies drug combinations and associated target adverse drug reaction from a spontaneous reporting system containing case reports of drugs and associated adverse drug reactions. Each drug combination comprises a first drug and a second drug, and a propensity score is computed for each drug in each group. This propensity score expresses a probability of being exposed to a given drug based on other co-prescribed drugs and reported indications, which reflect patient characteristics. Associations are computed for each drug as well as drug interaction. Among the associations, the sum of the associations of the second drug and the interaction effect represents the predicted beneficial score expressing whether the second drug alters the chance of developing the target adverse drug reaction for patients on the first drug. The interaction effect is referred to as predicted interaction score, and represents antagonistic or synergistic drug interactions.

18 Claims, 4 Drawing Sheets

(56) References Cited

PUBLICATIONS

D. Hare et al., "The Orange Book: The Food and Drug Administration's Advice on Therapeutic Equivalence"; American Pharmacy, Jul. 7, 1990; vol. NS30, pp. 35-37.
D.C. Malone et al.; "Assessment of potential drug-drug interactions with a prescription claims database"; Am J Health-Syst Pharm-vol. 62 Oct. 1, 2005, DOI 10.2146/ajhp040567 (Year 2005).
D.S. Wishart et al., "DrugBank: A Knowledgebase for Drugs, Drug Actions and Drug Targets", Nucleic Acids Research, 2008, vol. 36, Issue Suppl 1, pp. D901-D906.
E. Sakaida et al., "Safety of a Short Hydration Method for Cisplatin Administration in Comparison with a Conventional Method—a Retrospective Study"; Japanese Journal of Clinical Oncology, Jan. 10, 2016, pp. 370-377.
E.P. Van Puijenbroek et al.; "A comparison of measures of disproportionality for signal detection in spontaneous reporting systems for adverse drug reactions"; Pharmacoepidemiology and Drug Safety 2002; 11: 3-10, DOI: 10.1002/pds.668 (Year: 2002).
FDA, "Questions and Answers on FSA's Adverse Event Reporting System (FAERS)" (http://www.fda.gov/cder/aers/default.htm).
G.N. Norén et al., "A Statistical Methodology for Drug-Drug Interaction Surveillance"; Statistics in Medicine, 2008, 27, pp. 3057-3070.
H. Huang et al., "Systematic Prediction of Drug Combinations Based on Clinical Side-Effects", Scientific Reports, Nov. 24, 2014, pp. 1-7.
H. Iwata et al., "Large-Scale Prediction of Beneficial Drug Combinations Using Drug Efficacy and Target Profiles", Journal of Chemical Information and Modeling, 2015, vol. 55, pp. 2705-2716.
J. Henkel, "Attacking AIDS with a 'Cocktail' Therapy: Drug Combo Sends Deaths Plummeting", FDA consumer; Jul. 1, 1999.
J. Pearl, "The Foundations of Causal Inference", Sociological Methodology, Technical Report, R-355, Aug. 2010, pp. 1-76.
J.P. Guilford, "The Phi Coefficient and Chi Square as Indices of Item Validity", Psychometrika, vol. 6, No. 1, Feb. 1941, pp. 11-19.
K.P. Morgan et al., "The Role of Mannitol as a Nephroprotectant in Patients Receiving Cisplatin Therapy", The Annals of Pharmacotherapy, Feb. 2012, vol. 46, pp. 276-281.
M. Bansal et al., A Community Computational Challenge to Predict the Activity of Pairs of Compounds, Nature Biotechnology, Dec. 2014, vol. 32, No. 12, pp. 1213-1222.
M. Hauben et al., "Evidence of Misclassification of Drug-Event Associations Classified as Gold Standard 'Negative Controls' by the Observational Medical Outcomes Partnership (OMOP)", Drug Safety, Feb. 15, 2016.
M. Kanehisa et al., "KEGG for Representation and Analysis of Molecular Networks Involving Diseases and Drugs", Nucleic Acids Research, Jan. 2010, vol. 38, Database issue, pp. D355-D360.
M. Kuhn et al., "A Side Effect Resource to Capture Phenotypic Effects of Drugs", Molecular Systems Biology 6, Article No. 343, 2010, pp. 1-6; EMBO and Macmillian Publishers Limited.
M. Kuhn et al., "STITCH: Interaction Networks of Chemicals and Proteins", Nucleic Acids Research, 2008, vol. 36, pp. D684-D688.
M.R. Costanzo et al.; "The safety of intravenous diuretics alone versus diuretics plus parenteral vasoactive therapies . . . "; American Heart Journal, doi:10.1016/j.ahj.2007.04.033, Aug. 2007 (Year: 2007).
Medical Dictionary for Regulatory Activities (MedDRA). (http://www.meddra.org).
N.P. Tatonetti et al., "Detecting Drug Interactions from Adverse-Event Reports: Interaction Between Paroxetine and Pravastatin Increases Blood Glucose Levels", Clinical Pharmacology & Therapeutics, Jul. 2011, vol. 90, No. 1 pp. 133-142.
N.P. Tatonetti et al.; "A novel signal detection algorithm for identifying hidden drug-drug interactions in adverse event reports"; Am Med Inform Assoc 2012; 19: p. 79-85. doi:10.1136/amiajnl-2011-000214, Published Online First Jun. 14, 2011 (Year: 2011).
N.P. Tatonetti et al.; "Data-Driven Prediction of Drug Effects and Interactions"; Science Translational Medicine (ISSN 1946-6242, Mar. 14, 2012 vol. 4 Issue 125 125ra31 (Year: 2012).
N.P. Tatonetti, "Data-driven Prediction of Drug Effects and Interactions", Columbia University Medical Center, Apr. 26, 2013, pp. 1-105.
P. Li et al., "Large-scale Exploration and Analysis of Drug Combinations"; Bioinformatics, Feb. 8, 2015, 31, pp. 2007-2016.
P.B. Ryan et al., "Defining a Reference Set to Support Methodological Research in Drug Safety", Drug Safety, 2013, 36, Suppl 1, pp. 33-47.
P.M. Coloma et al., "A Reference Standard for Evaluation of Methods for Drug Safety Signal Detection Using Electronic Healthcare Record Databases", Drug Safety, Nov. 23, 2012, Springer International Publishing.
P.N. Valenstein, M.D., "Evaluating Diagnostic Tests with Imperfect Standards", American Journal of Clinical Pathology, 1990, vol. 93, pp. 252-258.
R. Harpaz et al., "Mining Multi-item Drug Adverse Effect Associations in Spontaneous Reporting Systems", BMC Bioinformatics, 2010, Issue 11, Supplement 9, pp. 1-8.
S. Ayvaz et al., "Toward a Complete Dataset of Drug-Drug Interaction Information from Publicly Available Sources", Journal of Biomedical Informatics, 2015, vol. 55, pp. 206-217.
S. Zhao et al., "Systems Pharmacology of Adverse Event Mitigation by Drug Combinations", National Institute of Health, NIH-PA Author Manuscript, Sci Transl Med., Oct. 9, 2013, pp. 1-19.
S.K. Misra et al., "Combinatorial Therapy for Triple Negative Breast Cancer Using Hyperstar Polymer-based Nanoparticles", Chemical Communications, 51, Dec. 4, 2015, pp. 16710-16713.
T. Klein et al., "Integrating Genotype and Phenotype Information: an Overview of the PharmGKB Project", The Pharmacogenomics Journal, 2001, vol. 1, pp. 167-170.
V. Law et al., "DrugBank 4.0: Shedding New Light on Drug Metabolism"; Nucleic Acids Research, Nov. 6, 2013, 42, pp. D1091-D1097.
X. Li et al., "The Efficacy and Safety of Aspirin Plus Dipyridamole Versus Aspirin in Secondary Prevention Following TIA or Stroke: A Meta-analysis of Randomized Controlled Trials", Journal of the Neurological Sciences, 332, 2013, pp. 92-96.
List of IBM Patents or Patent Applications Treated as Related.

DATA-DRIVEN PREDICTION OF DRUG COMBINATIONS THAT MITIGATE ADVERSE DRUG REACTIONS

CROSS REFERENCE TO RELATED APPLICATIONS

The present application is a continuation of, and claims the benefit of priority of, U.S. patent application Ser. No. 15/257,535, filed Sep. 6, 2016, titled "Data-Driven Prediction of Drug Combinations That Mitigate Adverse Drug Reactions," the entire contents of which are incorporated herein by reference.

FIELD OF THE INVENTION

The present invention relates to combinatorial drug therapy.

BACKGROUND OF THE INVENTION

Combinatorial drug therapy is useful for combating complex and refractory diseases such as acquired immune deficiency syndrome (AIDS), cancer and Type 2 diabetes mellitus (T2DM). Combinations of drugs work synergistically to improve therapeutic efficacy or work antagonistically to alleviate the risk of adverse drug reactions. For example, the combined use of aspirin and dipyridamole has been shown to be more beneficial and safer than using either of the drugs alone for secondary prevention of stroke. Despite the increasing number of drug combinations used, a significant challenge remains in discovering beneficial drug-drug combinations (DDCs) in a scalable manner. Most combinations are found in a clinical setting through experience or are experimentally derived by dose-response curves for a pair of drugs against a protein target. Recently, sources of large-scale data on drugs have been created that include detailed chemical, pharmacological, and pharmaceutical data along with sequence, structure, and pathway information about drug targets.

While the identification of novel DDCs is expected to contribute to the development of combinatorial drug therapy, existing studies are based on in-vitro experimental data, data collected from a limited number of participants in clinical trials or data from limited well-known drug combinations extracted from the Food and Drug Administration (FDA) orange book. Spontaneous reporting systems (SRSs) routinely collect drug-induced adverse drug events (ADEs) from patients on single medication or complex combinations of medications, which provide an opportunity to discover unexpected beneficial drug combinations for ADE reduction. Researchers have used SRSs to identify drug combinations that lead to unanticipated harmful adverse events, hereinafter referred to as drug-drug interactions (DDIs), and developed methodologies to effectively mine this database. For example, one researcher implemented a three-way disproportionality measure to identify suspected DDIs, and evaluated the method using empirical examples among the 20 highest predictions. Another researcher used association rule mining to identify multi-item ADE associations from the FDA adverse event reporting systems (FAERS), and 4% of results were characterized and validated as DDIs by an expert. Another attempt at utilizing FAERS reports mined these reports for side-effect profiles related to glucose homeostasis and uncovered a novel interaction between pravastatin and paroxetine that causes a potentially hazardous increase in blood glucose levels.

In theory, both adverse drug combinations (DDIs) and beneficial drug combinations (DDCs) resulting in ADE reduction should be obtainable from SRSs. A proposed method to identify DDCs based on FAERS utilized difference-in-differences estimators to look for drug pairs in which a second drug, i.e., Drug B, when taken with a first drug, i.e., Drug A, could reduce reports of adverse events from patients taking Drug A. For example, the combined therapy of rosiglitazone and exenatide reduced the reported incidences of myocardial infarction associated with the use of rosiglitazone alone.

A known issue with SRS data is selection biases resulting from the nonrandom selection of subjects that are exposed to the drug and that experience adverse events. This selection bias could lead to many false positive associations between the drug and the ADR when a causative covariate, e.g., a patient's disease state or other medications, is not taken into account. In order to alleviate such bias, an extensive post-hoc analysis is conducted based on stratification of the data on predefined covariates such as the use of metformin and Type 2 diabetes. However, such stratification requires significant domain knowledge and sometimes enumeration of important covariates, which is intractable for any large-scale analysis. Propensity score matching (PSM) is the most developed and popular strategy for causal analysis in observational studies that yield an unbiased estimate of treatment effects. The PSM for single drug-ADR detection has been successfully applied, and results showed that PSM can reduce selection bias associated with drugs reported in the case reports, decreasing the false positive associations.

SUMMARY OF THE INVENTION

Exemplary embodiments are directed to systems and methods for the prediction of drug combinations where one drug reduces the ADRs of the other. The drug combinations are predicted based on data from SRSs. The predictive model constructs a known drug-drug interaction (DDI) reference standard and was applied to perform large-scale screening on SRS data for drug-ADR-drug triples where polypharmacy could potentially reduce the ADR. Analysis of the top ranking candidates showed a high level of clinical validity.

Exemplary embodiments are directed to a method for large-scale prediction of drug combinations where one or more second drugs are identified that could be co-prescribed with a first drug to reduce the rate or incidence of adverse drug reactions associated with the first drug. The second drugs are identified using SRSs and can be outputted as list ranked in accordance with the likelihood of level of reduction in adverse drug reactions. In one embodiment, first and second drug combinations are linked to the beneficial clinical effects of the combination. For example, the combined use of the second drug with the first drug can reduce the rate of a given health condition such as heart attack. Therefore, exemplary embodiments provide more than merely a binary indication of efficacy, i.e., yes or no.

Exemplary embodiments are directed to a method for predicting beneficial drug combinations that mitigate adverse drug reactions. This method identifies a candidate set of drug combinations and target adverse drug reaction from at least one spontaneous reporting system containing case reports of drugs and associated adverse drug reactions. Each drug combination in the candidate set of drug combinations has a first drug associated with increasing a rate of occurrence of a given target adverse drug reaction and a second drug capable of reducing the rate of occurrence of the given target adverse drug reaction induced by the first drug. In one embodiment, the case reports in each spontaneous reporting system are pre-processed to remove extra characters, identify generic names, identify brand names, identify clinical program names, correct misspellings, remove foreign names, replace foreign names, aggregate drugs under a single ingredient name, format data, upload data in a desired data format, generate summary statistics for the case reports in the spontaneous reporting system and combinations thereof.

Initially, a set of first drug and target adverse drug reaction pairs are identified such that each first drug and targeted adverse drug reaction pair comprises at least a threshold number of entries in the case reports. In one embodiment, the threshold number of entries comprises 200 entries. Next, first drug and target adverse drug reaction pairs in the set of first drug and target adverse drug reaction pairs are identified having an odds ratio of developing a given adverse drug reaction as a result of a given first drug over a background level of developing the given adverse reaction that is significantly greater than one by a statistically significant amount. Suitable methods for determining if the odds ratio of developing a given adverse drug reaction as a result of a given first drug over a background level of developing the given adverse reaction is significantly greater than one by a statistically significant amount include, but are not limited to, using a Chi-square test.

Each identified first drug and target adverse drug reaction pair in the second set of first drug reaction pairs having the odds ratio greater than one by the statistically significant amount is compared to a database of known drug side effects, and first drug and target adverse drug reaction pairs are removed from the set of first drug and target adverse drug reaction pairs that are not listed in the database of known drug side effects. Second drugs are identified for each first drug and target adverse drug reaction pair in the set of first drug and target adverse drug reaction pairs such that each identified second drug appears with the first drug for any given adverse drug reaction in at least a threshold number of case reports. In one embodiment, the threshold number of case reports is 500.

A propensity score for each first and second drug in each drug combination. This propensity score is a probability of being exposed to each first and second drug based on a given set of patient characteristics. In addition, at least one of associations between being prescribed a given first drug or second drug and developing a given target adverse drug reaction and interactions between the first drug and the second drug that affect the rate of occurrence of the given target drug reaction are computed. In one embodiment, the computed propensity scores are used in a regularized logistic regression, and coefficients from the regularized logistic regression are used to calculate a predicted beneficial score that expresses whether adding the second drug would alter the rate of occurrence of developing the target adverse drug reaction and a predicted interaction score expressing whether the second drug will interact with the first drug to alter the rate of occurrence of the target adverse drug reaction. In one embodiment, a ranked list of second drugs from the identified plurality of groups is outputted. The second drugs are ranked according to an ability to reduce first drug induced adverse drug effects. In one embodiment, links between drug combinations in the plurality of groups of drug combinations and target adverse drug reactions and beneficial clinical effects resulting from the use of the second drug are identified.

Exemplary embodiments are also directed to a computing system for predicting beneficial drug combinations. The computing system includes a hardware memory storing a database containing at least one spontaneous reporting system with a plurality of case reports of drugs and associated adverse drug reactions. A processing unit is provided in communication with the memory. A selection module identifies a candidate set of drug combinations and target adverse drug reaction from at least one spontaneous reporting system containing case reports of drugs and associated adverse drug reactions. Each drug combination in the candidate set of drug combinations includes a first drug associated with increasing a rate of occurrence of a given target adverse drug reaction and a second drug capable of reducing the rate of occurrence of the given target adverse drug reaction induced by the first drug. A propensity score module computes a propensity score for each first and second drug in each drug combination. The propensity score is a probability of being exposed to each first and second drug based on a given set of patient characteristics. In addition, an associations module computes at least one of associations between being prescribed a given first drug or second drug and developing a given target adverse drug reaction and interactions between the first drug and the second drug that affect the rate of occurrence of the given target drug reaction.

In one embodiment, the computing system also includes a filtering module configured to filter the case reports in the spontaneous reporting system to generate a reduced search space within the spontaneous reporting systems. This filtering module includes a first drug and linked adverse drug reaction pair identification module to identify a set of first drug and target adverse drug reaction pairs such that each first drug and targeted adverse drug reaction pair is found in at least a threshold number of entries in the case reports and to identify first drug and target adverse drug reaction pairs in the set of first drug and target adverse drug reaction pairs having an odds ratio of developing a given adverse drug reaction as a result of a given first drug over a background level of developing the given adverse reaction that is significantly greater than one by a statistically significant amount. A known side effects comparison module compares each identified first drug and target adverse drug reaction pair in the second set of first drug reaction pairs having the odds ratio greater than one by the statistically significant amount to a database of known drug side effects and removes first drug and target adverse drug reaction pairs from the set of first drug and target adverse drug reaction pairs that are not listed in the database of known drug side effects. A second drug identification module identifies second drugs for each first drug and target adverse drug reaction pair in the set of first drug and target adverse drug reaction pairs such that each identified second drug appears with the first drug for any given adverse drug reaction in at least a threshold number of case reports regardless of the adverse drug reaction. In addition, the second drug identification module uses the computed propensity scores in a regularized logistic regression and uses coefficients from the regularized logistic regression to calculate a predicted beneficial score that expresses whether adding the second drug would alter the rate of occurrence of developing the target adverse drug reaction and a predicted interaction score expressing whether the second drug will interact with the first drug to alter the rate of occurrence of the target adverse drug reaction.

DETAILED DESCRIPTION

Figure 1:
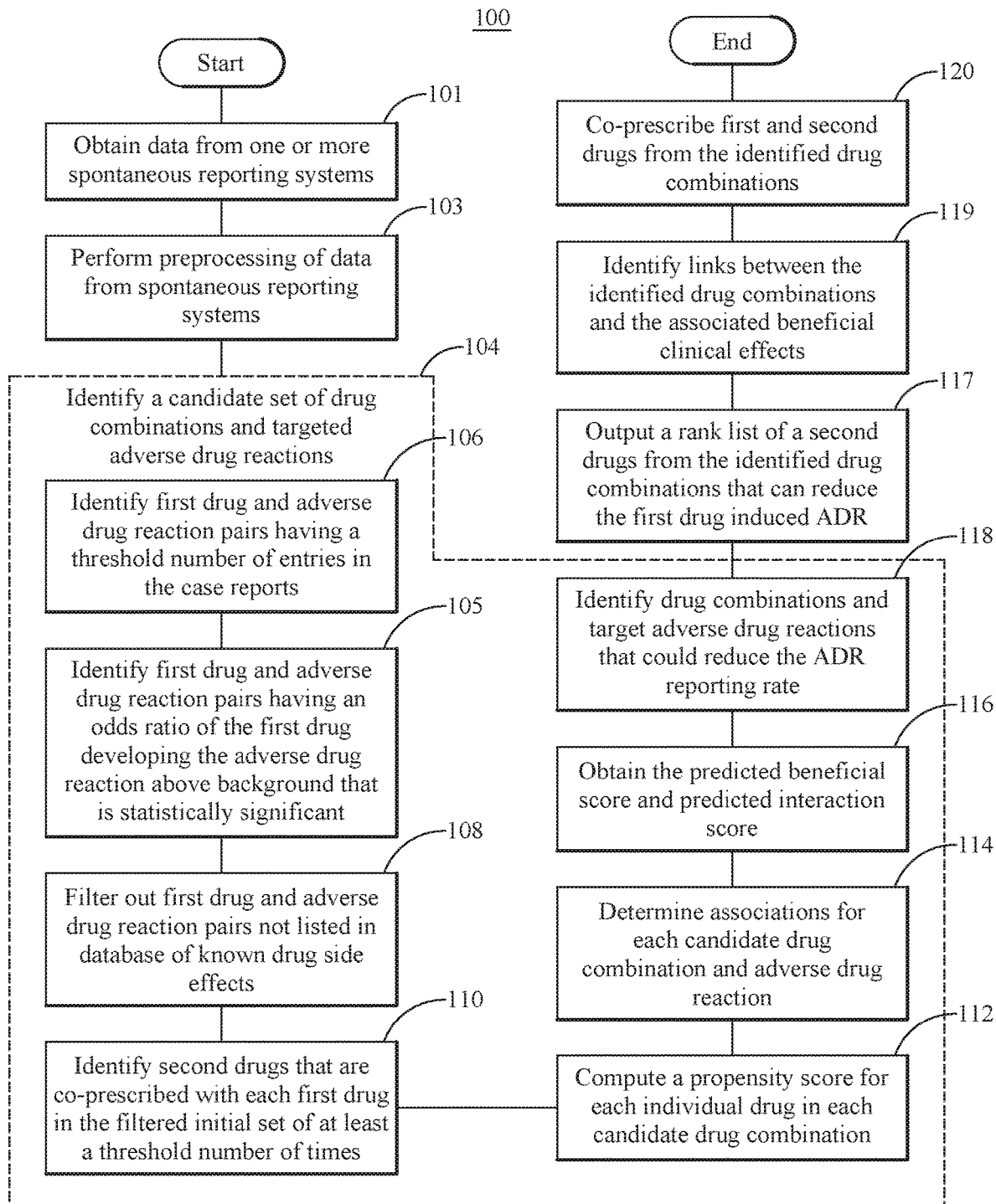
FIG. 1 is a flow chart illustrating an embodiment of a method for predicting beneficial drug combinations from spontaneous reporting systems.

Exemplary embodiments include a data-driven method, which incorporates propensity score matching (PSM), for large-scale prediction of drug combinations where one drug could reduce the adverse drug reactions (ADRs) of the other, based on, for example, food and drug administration (FDA) adverse event reporting systems (FAERS) data. A first drug, denoted as Drug A, is identified as a medication that could cause a specific ADR, and a second drug, denoted as Drug B, is identified as a medication that could reduce the reported rate of Drug A-induced ADR. Drug B can alter the chance of developing Drug A-induced ADR through two mechanisms, the additive or subtractive individual effect of Drug B itself and the interactive effect with Drug A. A combined effect of Drug A and Drug B is predicted that considers both mechanisms. Since both beneficial and harmful drug interactions are of interest, results associated with the interaction effect alone are reported.

The knowledge, i.e., ground truth, of beneficial drug combinations in terms of ADR reduction is limited or nonexistent. Therefore, exemplary methods are evaluated based on a reference standard of known drug-drug interactions (DDIs) and their related ADRs, which is a practice known in pharmacovigilance. Suitable data sources include, but are not limited to, FAERS, Side Effect Resource (SIDER) and DrugBank. FAERS is a spontaneous reporting system maintained by the U.S. Food and Drug Administration. FAERS contains case reports of suspected ADRs, which are either obligatorily submitted by pharmaceutical companies or are voluntarily reported by healthcare professionals and consumers. Drugs are entered in a report using free text, which can include brand or generic names, while suspected ADRs are coded using the Medical Dictionary for Regulatory Activities (MedDRA) terms. In addition, some reports link the medications to their indications, which are also coded using MedDRA terms. In one embodiment to gain statistical power, the drug names are normalized to their chemical compounds using the search tool for interactions of chemicals (STITCH) database, which maintains synonym lists for chemicals, and relationships between drugs and their chemical compounds. For example, quinapril hydrochloride and hemokvin are mapped to the main or active ingredient quinapril.

The SIDER database is a publicly available resource that relates the medications to their known side effects, or ADRs. The relationships are extracted by an automatic method from the FDA Structured Product Labels. Presently, the medications are coded using STITCH, and the ADRs are coded using MedDRA terms. For instance, the medication lasofoxifene (CID000216416) is described to cause the MedDRA-coded side effect gastrointestinal pain. SIDER is available in various versions, and the latest version is SIDER 4.1.

The DrugBank database is a comprehensive knowledgebase for drugs, drug actions, and drug targets that contains detailed biomedical and pharmacological information about drugs, their mechanisms and their targets. In addition, DrugBank provides a set of 12,128 ingredient level drug-drug interactions (DDIs), most of which include a brief textual description of the interaction. For example, an interaction between nalidixic acid and warfarin is described as "nalidixic acid may increase the anticoagulant effect of warfarin". Another entry states that "the combined use of amiodarone and lovastatin increase the risk of severe myopathy/rhabdomyolysis", which links the DDI between amiodarone and lovastatin to its ADRs of myopathy or rhabdomyolysis that can be mapped to MedDRA terms. DrugBank is available in various versions including version 4.0.

Referring initially to FIG. 1, an exemplary embodiment of a method for predicting beneficial drug combinations from spontaneous reporting systems 100 is illustrated. According to this method, data are obtained from one or more spontaneous reporting systems (SRSs) 101. Suitable spontaneous data systems include, but are not limited to, FAERS. The spontaneous reporting systems record drug-induced adverse events for both single drugs and combination therapies. A given spontaneous reporting system can include millions of entries submitted by patients, physicians, hospitals, lawyers and drug companies. The data in a given spontaneous reporting systems comprises a plurality of event entries, with each event entry comprising at least one drug and an associated adverse event. Each event entry can include information regarding patient characteristics and dosage as well as severity and duration of the adverse drug reaction. The data can be formatted in any suitable computer or machine readable format, for example, American Standard Code for Information Interchange (ASCII).

In one embodiment, the data from each spontaneous reporting system is pre-processed automatically. Suitable pre-processing includes removing extra characters, identifying generic names, identifying brand names, identifying clinical program names, correcting misspellings and removing or replacing foreign names. In one embodiment, a given drug or drug name is aggregated under a single ingredient name. Having pre-processed the data, the processed data, or processed reports are formatted or uploaded in the desired data format. In one embodiment, summary statistics for the data in the spontaneous reporting system are generated. These summary statistics include, but are not limited to, the total number of case reports or events, the total number of drugs reported, and the total number of different adverse drug reactions reported.

Exemplary embodiments use data from the spontaneous reporting systems to identify unexpected beneficial drug combinations, i.e., beneficial in reducing the rate of adverse drug reactions. In one embodiment, a candidate set of drug combinations and target adverse drug reaction is identified 104 from at least one spontaneous reporting system containing case reports of drugs and associated adverse drug reactions. Each drug combination in the candidate set of drug combinations is a first drug associated with increasing a rate of occurrence of a given target adverse drug reaction and a second drug capable of reducing the rate of occurrence of the given target adverse drug reaction induced by the first drug. Each spontaneous reporting system contains a plurality of case reports of drugs and associated adverse drug reactions. Candidate drug combination and targeted adverse drug reaction are identified in the data from the spontaneous reporting system. In one embodiment, a plurality of candidate drug combinations is identified. Each candidate drug combination contains two drugs. As used herein, the targeted adverse drug reaction is an adverse drug reaction associated with one of the drugs in a given candidate drug combination and is targeted for improvement, compensation or correction by the additional drug in each candidate drug combination. In one embodiment, multiple targeted adverse drug reactions can be identified, each associated with one drug in the candidate drug combination, and each adverse drug reaction is targeted for improvement by the additional drugs in the candidate drug combination. In one embodiment, each candidate drug combination includes a first drug, Drug A, associated with a given ADR, which is the targeted adverse drug reaction, and a second drug, Drug B. Therefore, each candidate drug combination and targeted adverse drug reaction defines a candidate triple of Drug A-ADR-Drug B.

In order to obtain the candidate drug combinations and their targeted ADR, a multi-step or multi-criteria process incorporating a statistical method is used to filter the candidate drug combinations and targeted adverse drug reactions. In one embodiment, the process and statistical method are applied to potential candidate triples, e.g., Drug A-ADR-Drug B, although the three step process and statistical method can be used to filter other combinations of potential candidate drug combinations and adverse drug reactions. The three criteria in combination with the statistical method limit the search space by filtering the potential candidate drug combinations and targeted adverse drug reactions to create a set of candidate drug combinations and adverse drug reactions, e.g., Drug A-ADR-Drug B triples. The first criterion identifies first drug and linked adverse drug reaction pairs, e.g., pairs of Drug A-ADR, having at least a threshold number of entries in the database, e.g., FAERS, and an associated odds of the first drug developing the adverse drug reaction above a pre-defined level 106. In one embodiment, all pairs of Drug A-ADR reported in the FAERS case report data more than 200 times are identified.

In the next step, first drug and target adverse drug reaction pairs in the set of first drug and target adverse drug reaction pairs are identified having an odds ratio of developing a given adverse drug reaction as a result of a given first drug over a background level of developing the given adverse reaction that is significantly greater than one by a statistically significant amount 105. Candidate pairs of Drug A-induced ADR are identified based on the observed Odds Ratio (OR). For Drug denoting a Drug A, the OR of Drug developing an ADR is defined as:

$$OR_{ADR,Drug} = \frac{\text{Odds}(ADR = 1 \mid \text{Drug} = 1)}{\text{Odds}(ADR = 1 \mid \text{Drug} = 0)} \quad (1)$$

$$\text{where odds } (X) = \frac{Pr(x)}{1 - Pr(x)}.$$

An OR greater than 1 indicates the chance that Drug develops the ADR is higher than the expected background rate, and an OR smaller than 1 indicates the chance that Drug develops the ADR is lower than the expected background rate. By replacing the probabilities in (1) with empirical probabilities, the observed OR for each Drug A-ADR pair is obtained. For each OR determined to be greater than 1, a determination is made regarding whether that OR is greater than 1 by a statistically significant amount. In one embodiment, the Chi-Square test is used to determine whether the observed OR for a given Drug-ADR pair is significantly greater than 1. The Chi-Squared test is used to calculate a p-value, and any Drug A-ADR pair with p-value less than 0.05 are selected into the initial set of Drug A-ADR pairs. Therefore, the filtered first drug and adverse drug reaction pairs are produced.

The third criterion further filters the initial set of filtered first drug and adverse drug reaction pairs by filtering out of the initial set those pairs not mentioned in one or more databases of known drug side effects 108. Suitable databases of known drug side effects include, but are not limited to, SIDER, for example, version 4.1. In one embodiment, each identified first drug and target adverse drug reaction pair in the second set of first drug reaction pairs having the odds ratio greater than one by the statistically significant amount are compared to the database of known drug side effects. First drug and target adverse drug reaction pairs are removed from the set of first drug and target adverse drug reaction pairs that are not listed in the database of known drug side effects.

The fourth criterion selects, for each first drug and adverse drug reaction pair in the filtered initial set, at least one second drug, e.g., Drug B, or a plurality of second drugs, such that each second drug has been co-prescribed with the first drug for at least a threshold number of co-prescriptions 110. In one embodiment, each second drug has been co-prescribed at least 500 times, i.e., a minimum of 500 case reports exist in the database. In one embodiment, selection of each second drug is made regardless of any association between the second drug and any target adverse drug reaction. In an embodiment where the first drug, target adverse drug reaction and second drug form a candidate drug triple, all candidate Drug A-ADR-Drug B triples are expressed as $C = \{(\text{Drug A, ADR, Drug B})\}$, and elements in C are denoted as $C_i$.

To identify the candidate set of drug combinations and targeted adverse drug reactions, a propensity score is computed for each first and second drug in each drug combination. The propensity score reflects a probability of being exposed to each first and second drug based on a given set of patient characteristics. Therefore, in one embodiment, a propensity score is calculated for each individual drug in each candidate drug combination 112. For candidate drug A-ADR-drug B triples, propensity scores are calculated for individual drugs in each triple, i.e., each first and second drug in each $C_i$. The calculated propensity score is the conditional probability of being exposed to a given drug, given a set of patient baseline characteristics. These baseline characteristics include drugs that patients are on and indications associated with the patients. Using propensity scores, potential bias due to treatment selection is mitigated and the response being evaluated is conditionally independent given the measured baseline characteristics. In one embodiment, to adjust potential selection bias a propensity score is calculated for each individual drug that is either Drug A or Drug B in C. For each individual drug, the baseline characteristics are selected as the top 200 most relevant medications and indications.

In one embodiment, the relevance of a medication or an indication to a drug is measured by the phi correlation coefficient. As used herein, Rx and Dx denote the relevant medications and indications respectively. To obtain the propensity score, a logistic regression is performed for each drug, which is expressed as the following:

$$\text{logit}(P(\text{Drug}=1)) = \alpha + \Sigma_{i=1}^{200} \delta_i R x_i + \Sigma_{j=1}^{200} \gamma_j D x_j \quad (2)$$

Where $\text{logit}(x) = \log(x/1-x)$ and $\alpha$, $\delta$ and $\gamma$ are the coefficients in the logistic regression. Once the estimates of the coefficients are obtained, the propensity score is estimated as the predicted probability of receiving the drug for each case report, i.e., predicted value of $P(\text{Drug}=1)$.

At least one of associations between being prescribed a given first drug or second drug and developing a given target adverse drug reaction and interactions between the first drug and the second drug that affect the rate of occurrence of the given target drug reaction can then be determined. In one embodiment, having determined the propensity score, associations for each candidate drug combination and targeted adverse drug reaction, e.g., each specific Drug A-ADR-Drug B triple, are determined 114. Therefore, an association between the use of Drug B in combination with Drug A on the likelihood of Drug A to develop the associated target ADR of interest is determined. For embodiments with Drug A-ADR-Drug B triples, the chance that Drug A develops the ADR of interest is higher than the expected background rate has been established through the filtering process for each triple, $C_i$=(Drug A,ADR,Drug B). Then a determination is made regarding how the chance developing the target ADR of interest is altered by adding the second medication, i.e., Drug B, in combination with the first medication, i.e., Drug A. This determination of altering the chance of developing the target ADR of interest given the addition of the second medication is determined using two separate predicted scores. The first predicted score is the predicted beneficial score for taking Drug B, i.e., given that the patient is prescribed with Drug A, whether adding Drug B will modify the chance of developing the ADR of interest. The second predicted score is the predicted interaction score, i.e., given that the patient is prescribed both Drug A and Drug B, whether Drug B will interact with Drug A to alter the chance of developing the ADR of interest.

In one embodiment, the two predicted scores are generated by a regularized logistic regression as follows:

$$\text{logit}(P(\text{ADR}=1))=\beta_0+\beta_1 \text{Drug}A+\beta_2 P_1+\beta_3 \text{Drug}B+\beta_4 P_2+\beta_5 \text{Drug}A*\text{Drug}B+\lambda|\beta|_1 \quad (3)$$

Where $P_1$ and $P_2$ are the propensity scores for Drug A and Drug B, respectively, $\beta_i$ for i=0, ..., 5 are the coefficients, $\beta=(\beta_1, \beta_s)$ denotes the vector of linear coefficients, and $|*|_1$ denotes the L1 norm. The last term on the right hand side of Formula (3) is the least absolute shrinkage and selection operator (LASSO) regularizer, which could enforce estimates of $\beta$ to be sparse, and $\lambda$ is the tuning parameter of the regularizer. In one embodiment, for each $C_1$=(Drug A, ADR, Drug B), an optimal $\lambda$ is selected by 3-fold crossvalidation, and $P_1$ and $P_2$ are obtained from the computed propensities. The addition of propensity scores in the logistic regression mitigates the drug selection bias given other patient characteristics. The values of Drug A and DrugB in the logistic regression can be 1 or 0. A value of 1 indicates that a patient is taking the drug, and a value of 0 indicates that a patient is not taking a drug.

The value of ($\beta_3+\beta_5$) is the predicted beneficial score for taking Drug B. The predicted beneficial score specifies the degree that a patient who is on Drug A could benefit or suffer from taking Drug B for the target ADR of interest. A predicted beneficial score smaller than 0 indicates that patients who are on Drug A could benefit from taking Drug B in terms of reducing the target ADR of interest, and a predicted beneficial score greater than 0 indicates that patients who are on drug A cannot benefit from taking drug B in terms of reducing the target ADR of interest.

The value of $\beta_s$ is the predicted interaction score. A predicted interaction score smaller than 0 indicates an antagonistic interaction between Drug A and Drug B which decrease the chance of developing the ADR of interest, while a predicted interaction score greater than 0 signifies a synergistic interaction between Drug A and Drug B which increase the chance of developing the ADR of interest. The later scenario is referred to as DDIs. Therefore, the predicted beneficial score for taking Drug B and predicted interaction score are obtained from the associations 116. Then drug combinations and targeted adverse drug reactions are identified where at least one of the predicted beneficial score for taking Drug B and the predicted interaction score indicate that the second drug or medication can reduce the reporting rate of the targeted ADR due to, i.e., induced by, the first drug or medication 118.

Having identified one or more second drugs, i.e., Drug B, for each first drug and adverse drug reaction pairing based on the predicted beneficial score and the predicted interaction score a rank list of the second drugs from the identified drug combinations that can reduce first drug induced adverse drug reactions is outputted 117. In one embodiment, the top ranked second drugs provide the most significant or dramatic reduction in first drug induced adverse drug reactions. The ranked list of second drugs includes the values of the predicted beneficial score and the predicted interaction score or a ranking score based on those values. In one embodiment, links between each identified drug combination, i.e., each first and second drug, and associated clinical benefits are identified 119. For example, a given combination of drugs can be identified as providing a reduction in rate or severity of a given condition.

The identified drug combinations are then used, i.e., the first and second drugs are co-prescribed, when the first drug or medication is prescribed to a patient 120. The steps of identifying the potential candidate drug combinations, filtering, propensity computation and association determination for the predicted beneficial score for taking Drug B and predicted interaction score can be repeated as the spontaneous reporting systems are updated over time.

Exemplary embodiments identify one or more, e.g., a set, of second drugs or medications, i.e., Drug Bs that could reduce the reporting rate of first drug or medication, i.e., Drug A, induced ADRs. In order to evaluate the method for identifying the second drugs, a reference standard containing a list of second drugs that are known to or not known to reduce the first drug induced ADRs is required. However, such reference standards are scarce or nonexistent. Therefore, the effectiveness of methods in accordance with the present invention are evaluated quantitatively by assessing the predicted interaction score ($\beta_5$) against a set of known DDIs and their ADRs. Following common practice in pharmacovigilance, a reference standard is constructed that contains DDIs known to cause or not known to cause either of two serious ADRs: rhabdomyolysis and QT prolongation. The DDIs, known to be associated with either rhabdomyolysis or QT prolongation, were extracted from an existing database, for example, the DrugBank knowledgebase, that includes positive controls in the reference standard. For negative controls, drugs in the FAERS are randomly paired. These random pairings, however, excluded pairings that are known to interact with each other for any ADR. The same number of negative controls as the positive controls is selected from the drug pairs that were not excluded. Selecting equal representation of positive and negative controls avoids class imbalance that can bias performance metrics to favor a method that is calibrated towards true positive rates when a reference set predominantly contains positive controls or specificity (1−false positive rate) when negative controls predominate. To quantitatively assess the performances of the exemplary embodiments of the method for predicting beneficial drug combinations from spontaneous reporting systems, receiver operating characteristic (ROC) curves are generated. The ROC curves are graphical plots of true positive rate vs. false positive rate. The entire ROC curve is plotted by varying the threshold value or prediction score, above which the output is predicted as positive and negative otherwise. In addition, the area under ROC curve (AUC) is calculated.

EXAMPLES

FAERS data were collected from January 2004 to September 2015, accounting for 6,434,615 case reports. These case reports contained 9,315 unique STITCH coded drugs and 18,159 MedDRA coded unique adverse drug events (ADEs). On average, each report contained 3.5 different generic drugs, 2.2 different indications and 3.4 different ADEs. Referring to Table 1, statistics and examples of positive and negative controls in the reference standard for DDIs and their ADRs are illustrated. The reference standard was based on the DrugBank knowledgebase. For example, according to the DrugBank knowledgebase, the concurrent use of cisapride and tacrolimus may result in an increased risk of QT-interval prolongation. In total, 50 positive controls and negative controls were
generated for rhabdomyolysis, and 61 positive controls and negative controls were created for QT prolongation. The relevant MedDRA preferred term for two ADRs were also defined, which were rhabdomyolysis and electrocardiogram QT prolonged respectively.

Exemplary embodiments were used for the large-scale prediction of novel drug combinations and their ADR reduction. A candidate set of 694,957 Drug A-ADR-Drug B triples was selected are described herein. This candidate set included 449 Drug As, 895 ADRs and 947 Drug Bs. Among these candidates, 322,417 Drug A-ADR-Drug triples had predicted beneficial scores smaller than 0, indicating that polypharmacy could potentially reduce the ADR. As described herein, the predicted beneficial score $(\beta_3+\beta_5)$ indicates the degree that a patient who is on Drug A could benefit or suffer from taking Drug B for the ADR of interest, and the predicted interaction score $\beta_s$ specifies the degree of the interaction effect between Drug B and Drug A on the ADR. Using the cutoff of 0, Table 2 illustrates the statistics of drug effects on the ADRs of interest computed from the regularized regression model. After adjusting for patient characteristics, 95.6% of Drug A-ADR pairs were positively associated indicating that Drug A increases the reported rate of ADRs. In addition, 3.3%

TABLE 1

Statistics and examples of positive and negative controls of the reference standard for DDIs

| ADR | Rhabdomyolysis | QT prolongation |
|---|---|---|
| MedDRA preferred term used in FAERS | RHABDOMYOLYSIS | ELECTROCARDIOGRAM QT PROLONGED |
| Number of positive controls | 50 | 61 |
| Examples of the combined use of drugs associated with the ADR | atorvastatin_repaglinide simvastatin_amlodipine colchicine_fluvastatin | cisapride_tacrolimus methadone_trimipramine fluconazole_voriconazole |
| Number of negative controls | 50 | 61 |
| Examples of the combined use of drugs not known to interact | losartan_torasemide pravastatin_electrolytes atorvastatin_hydromorphone | sotalol_valsartan levofloxacin_doxorubicin hydroxyzine_haloperidol |

Figure 2:
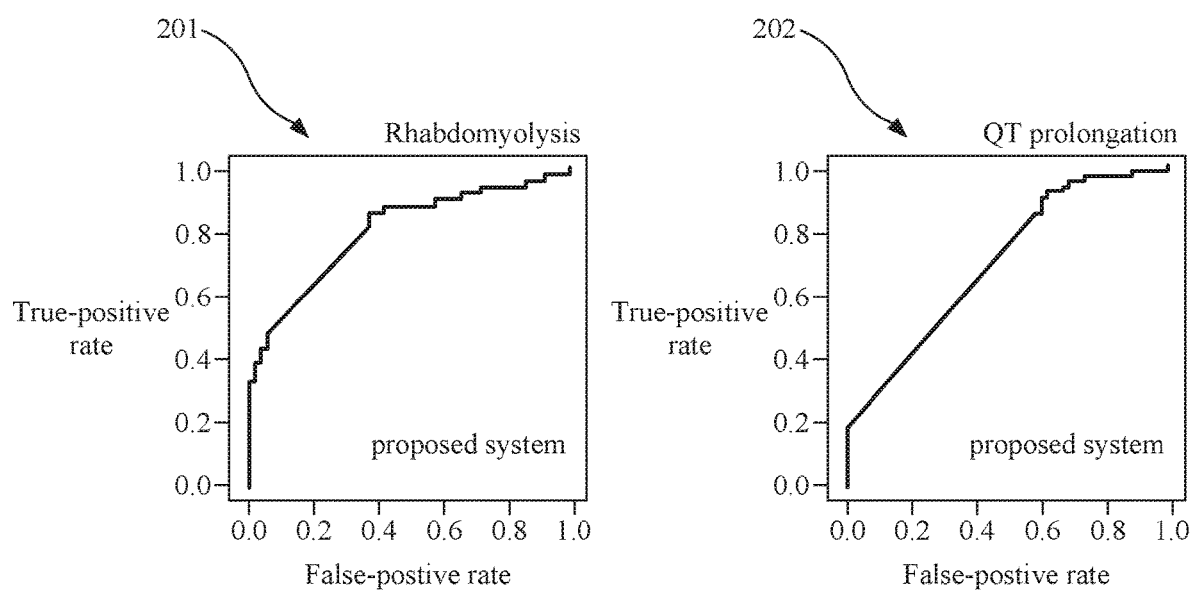
FIG. 2 is plots illustrating an embodiment of receiver operating characteristic curves for drug-drug interactions.

Referring to FIG. 2, the resulting ROC curves for the classification of 100 drug pairs for rhabdomyolysis 201 and 122 drug pairs for QT prolongation 202 are illustrated as true/false DDI using the proposed method. The AUC is 0.80 and 0.70 for rhabdomyolysis and QT prolongation respectively, where 1 indicates perfect classifier and 0.5 indicates random classifier. These AUC values indicate that exemplary methods are effective for identifying DDIs and their ADRs. Having determining the efficacy, exemplary methods are then used to identify second drugs (Drug Bs) that could reduce the target ADRs of the first drugs (Drug As).

of Drug A-ADR pairs were not associated indicating that Drug A does not either increase or decrease the reported rate of ADRs, and 1.1% of Drug A-ADR pairs were negatively associated indicating that Drug A decreases the reported rate of ADRs. Moreover, among all Drug A-ADR-Drug B triples, 46.4% of predicted beneficial scores were smaller than 0 indicating that taking Drug B could decrease the chance of developing the ADR induced by Drug A. In addition, 38.5% of predicted interaction scores were smaller than 0 signifying that Drug B could interact antagonistically with Drug A to reduce the ADR.

TABLE 2

Statistics of the drug effects on the ADR

| The effect of drug on the ADR (coefficient) | Increase the incidence of the ADR (coefficient > 0) | No association with the ADR (coefficient = 0) | Decrease the incidence of the ADR (coefficient < 0) |
|---|---|---|---|
| Drug A ($\beta_1$) | 95.6% | 3.3% | 1.1% |
| Predicted beneficial score ($\beta_3 + \beta_5$) | 34.3% | 19.3% | 46.4% |
| Predicted interaction score ($\beta_5$) | 14.6% | 46.9% | 38.5% |

Figure 3:
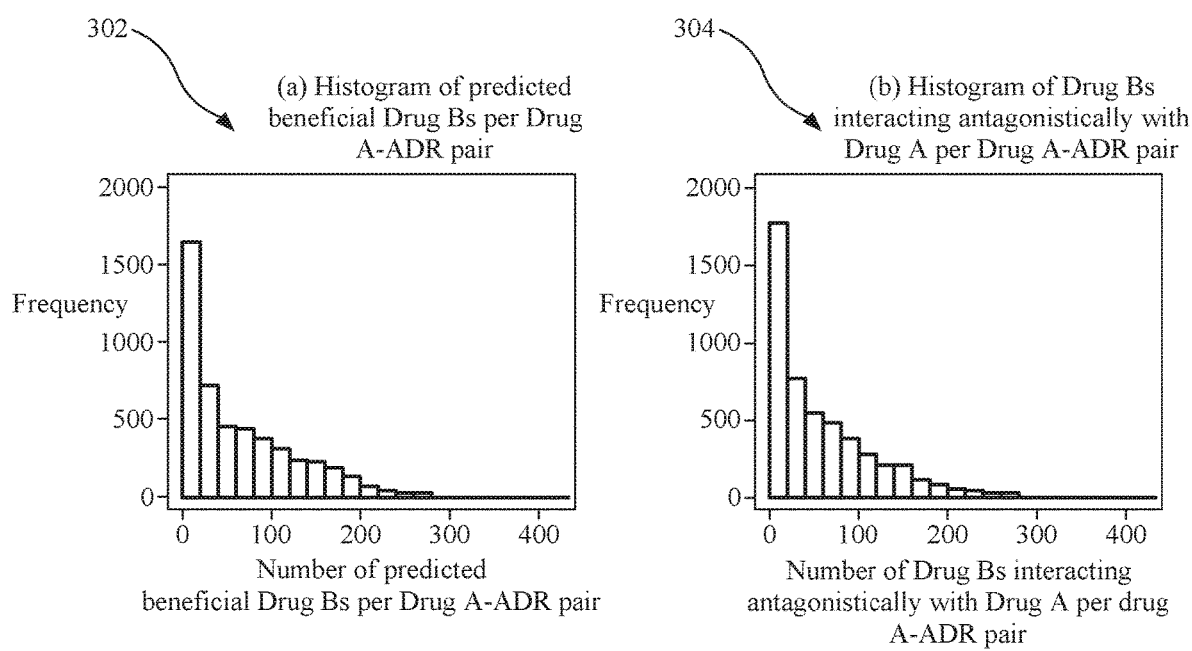
FIG. 3 are histograms illustrating predicted beneficial second drugs and predicted antagonistic second drug interactions with the first drug.

The negative values of predicted beneficial score and negative values of predicted interaction score are of interest. Referring to FIG. 3 a histogram of numbers of beneficial Drug Bs per Drug A-ADR pair 302 is illustrated. In total, the reporting rates of 4,950 drug A-induced ADRs can be reduced by at least one Drug B. On average, the reporting rate of a specific Drug A-induced ADR can be decreased by 65 Drug Bs. In addition, FIG. 3 illustrates the histogram of numbers of Drug Bs that could interact with Drug A antagonistically to reduce Drug A-induced ADR 304. In total, the reporting rates of 4,825 drug A-induced ADRs could be reduced by at least one Drug B's antagonistic interaction with Drug A. On average, the reporting rate of a specific drug A-induced ADR could be decreased by 55 Drug Bs.

TABLE 3

List of 15 predicted beneficial drug combinations and their ADR reduction

| Drug A name | ADRs associated with drug A | Drug B name | Predicted beneficial score | Common ATC code | Evidence for combined use |
| --- | --- | --- | --- | --- | --- |
| benazepril | DIZZINESS | amlodipine besylate | −0.57 | yes | F |
| atovaquone | PYREXIA | proguanil | −0.36 | yes | F |
| rofecoxib | MYOCARDIAL INFARCTION | pamidronate | −0.33 | yes | |
| rosiglitazone | MYOCARDIAL INFARCTION | exenatide | −0.32 | yes | |
| progesterone | BREAST CANCER | adalimumab | −0.27 | no | |
| trimethoprim | PYREXIA | sulfamethoxazole | −0.17 | yes | F |
| exemestane | ARTHRALGIA | everolimus | −0.16 | yes | III |
| amoxicillin | DIARRHOEA | clavulanic acid | −0.15 | yes | IV |
| ampicillin | PYREXIA | sulbactam | −0.15 | yes | F |
| desmopressin | HYPONATRAEMIA | somatropin | −0.15 | yes | |
| sertraline | ANXIETY | nicotinic acids | −0.14 | no | |
| sumatriptan | MIGRAINE | naproxen | −0.14 | no | F |
| olanzapine | DIABETES MELLITUS | biperiden | −0.13 | yes | |
| clindamycin | DIARRHOEA | benzoyl | −0.13 | yes | F |
| fluticasone | DYSPNOEA | salmeterol | −0.13 | yes | F |

The top 15 predictions were analyzed for two scores, and Table 3 displays a list of the top 15 Drug A-ADR-Drug B triples sorted with the predicted beneficial scores wherein the Drug B most dramatically reduced Drug A-induced ADR. As illustrated in Table 3, F denotes an FDA approved drug combination, III refers to a phase III clinical trial and IV refers to a phase IV clinical trial. In parallel, Table 4 presents a list of the top 15 Drug A-ADR-Drug B triples sorted by the predicted interaction scores wherein the drug B results in the best reduction of drug A-induced ADR. It was determined whether the predicted Drug B was prescribed with Drug A for the same disease using ATC code. Twelve Drug A-Drug B pairs in Table 3 and nine Drug A-Drug B pairs in Table 4 shared at least one ATC code signifying that the predicted drug combinations are useful in clinical practice since drug combinations are usually prescribed to treat or manage the same disease. The FDA orange book and clinical trials were interrogated to check clinical validity of the top ranked drug combinations. Nine drug combinations in Table 3 and two drug combinations in Table 4 have been validated in the orange book or investigated in the clinical trials, indicating their clinical validity.

TABLE 4

List of 15 predicted interacted drug combinations and their ADR reduction

| Drug A name | ADR associated with drug A | Drug B name | Predicted interaction score | Common ATC code | Evidence for combined use |
| --- | --- | --- | --- | --- | --- |
| niacin | FLUSHING | vitamin e | −0.34 | no | |
| rofecoxib | MYOCARDIAL INFARCTION | pamidronate | −0.31 | yes | |

TABLE 4-continued

List of 15 predicted interacted drug combinations and their ADR reduction

| Drug A name | ADR associated with drug A | Drug B name | Predicted interaction score | Common ATC code | Evidence for combined use |
|---|---|---|---|---|---|
| rosiglitazone | MYOCARDIAL INFARCTION | exenatide | −0.31 | yes | |
| progesterone | BREAST CANCER | adalimumab | −0.27 | no | |
| telaprevir | FATIGUE | peginterferon alfa-2b | −0.25 | no | III |
| lapatinib | DIARRHOEA | vinorelbine | −0.17 | yes | |
| exemestane | ARTHRALGIA | everolimus | −0.15 | yes | III |
| desmopressin | HYPONATRAEMIA | somatropin | −0.15 | yes | |
| clofarabine | FEBRILE NEUTROPENIA | cytarabine | −0.13 | yes | |
| finasteride | SEXUAL DYSFUNCTION | zoledronic acid | −0.12 | no | |
| liraglutide | NAUSEA | pioglitazone | −0.12 | yes | |
| midazolam | CARDIAC ARREST | pancuronium | −0.11 | yes | |
| olanzapine | DIABETES MELLITUS | levomepromazine | −0.11 | yes | |
| cisplatin | RENAL FAILURE ACUTE | Mannitol | −0.10 | no | |
| melphalan | NEUTROPENIA | Granisetron | −0.09 | no | |

III refers to a Phase III clinical trial

The results illustrated in FIG. 2 demonstrate that exemplary embodiments of the method are effective in identifying and prioritizing DDIs with their ADRs. By comparing Table 3 with Table 4, more clinical evidences were found for drug pairs when the overall beneficial effect of Drug B was considered. Typically, drug combinations are developed to aim at a more effective treatment than the monotherapy for a single disease such as the combined use of benazepril and amlodipine besylate, ranked 1 in Table 3, for treating hypertension and the combined use of atovaquone and proguanil, ranked 2 in Table 3, for treating or preventing malaria. However, very few clinical trials focus on evaluating the reduction of the Drug A-induced ADRs that the Drug B is able to achieve. Exemplary embodiments of the method for predicting beneficial drug combinations from spontaneous reporting systems show that the use of amlodipine besylate reduced benazepril-induced ADRs such as angioedema, cough and dizziness, with the most reduction in dizziness. Similarly, results show that the use of proguanil reduced atovaquone induced ADRs such as diarrhea, vomiting and pyrexia, with the most reduction in pyrexia. Cisplatin-acute renal failure-mannitol triple in Table 4 is an example that mannitol is used to reduce the chance of acute renal failure (ARF) with the use of cisplatin. Although a couple of studies have reached different conclusions about additional use of mannitol, either leads to reduction in the incidence of nephrotoxicity or is associated with the null result. These results show that mannitol could reduce ARF through an antagonistic interaction with cisplatin.

Similar to DDI detection task wherein very few of publicly available data sources linking the potential DDIs to their ADRs, very few of mined DDC data sources link DDCs to their beneficial clinical effects. For example, the study conducted by Iwata et al., "Prediction of Beneficial Drug Combinations Using Drug Efficacy and Target Profiles", Journal of Chemical Information and Modeling, 55:2705-2716 (2015), only predicted that the combined use of adrenaline and chloroprocaine was beneficial without relating them to a specific clinical effect. The predicted data set in accordance with exemplary embodiments is capable to relate DDCs to their clinical effects.

Exemplary embodiments provide a data-driven method for large-scale prediction of drug combinations where one drug could reduce the ADRs of the other, based on the FAERS data set. Exemplary embodiments are validated against a known DDI reference standard and are applied to perform large-scale screening on FAERS data for drug-ADR-drug triples where polypharmacy could potentially reduce the ADR. Analysis of the top ranking candidates demonstrated high level of clinical validity and the usefulness of the approach.

Figure 4:
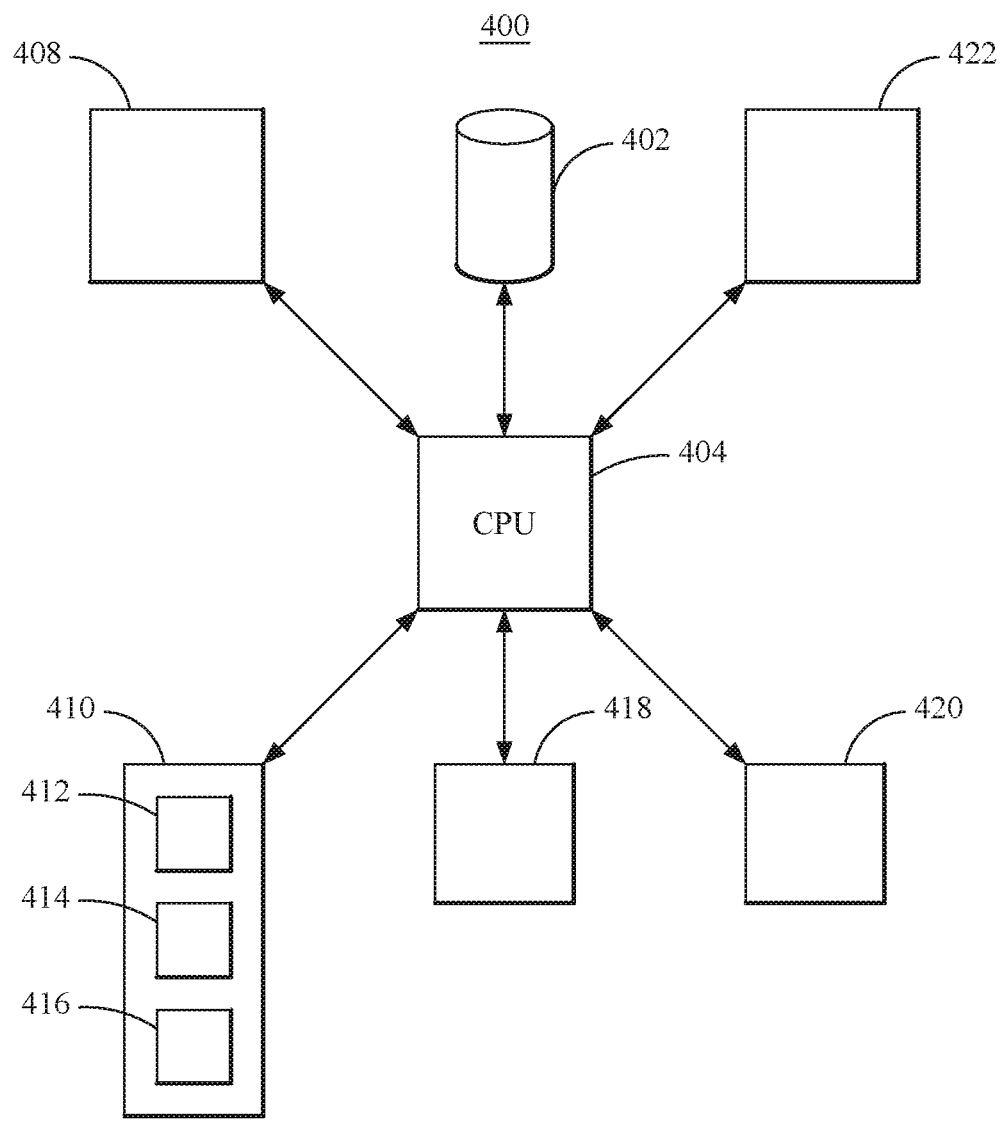
FIG. 4 is a schematic representation of an embodiment of a computing system for use in predicting beneficial drug combinations from spontaneous reporting systems.

Referring now to FIG. 4, exemplary embodiments are directed to a computing system for predicting beneficial drug combinations from spontaneous reporting systems. Suitable computing systems include stand-alone computers and computing systems, peer-to-peer based computing systems, individual servers, multiple servers and distributed computing systems. The various components of the computing system can communicate across one or more networks including local area networks and wide area networks. The computing system is executing instances of one or more software programs to provide the desired operations and modules for predicting beneficial drug combinations from spontaneous reporting systems. In addition, the computing system can also generate knowledge regarding beneficial first and second drug interactions from underlying data available, for example, from spontaneous reporting systems.

The computing system includes or has access to at least one hardware memory 402 containing one or more databases. The databases store data from the spontaneous reporting systems, biomedical and pharmacological information about drugs, their mechanisms and their targets, known drug side effects, medical dictionaries, medical codes, chemical dictionaries and chemical interaction databases. In addition the databases store the software code that when executed by the computing system provides the desired functionalities for predicting beneficial drug combinations from spontaneous reporting systems. In one embodiment, the databases store the outputs and knowledge generated by the computing system. The computing system includes at least one processing unit 404 in communication with the memory. The processing unit can execute the software code and provide the functionality of the various modules of the computing system.

In addition, the modules include a pre-processing module 408. The processing unit obtains the desired data from the memory and provides these data to the pre-processing module. The pre-processing module processes the data obtained from the spontaneous reporting systems to remove extra characters, identify generic names, identify brand names, identify clinical program names, correct misspellings and remove or replace foreign names. The pre-processing module can also aggregate drugs under a single ingredient name, format or upload data in the desired data format and generate summary statistics for the data in the spontaneous reporting system.

The processor then communicates the pre-processed data to a selection module and filtering module 410 configured to filter that data from the spontaneous reporting systems for identifying a plurality of groups of drug combinations and target adverse drug reaction from at least one spontaneous reporting system. The filtering module filters combinations of potential candidate drug combinations and adverse drug reactions from the preprocessed data. The filtering module includes a first drug and linked adverse drug reaction pair identification module 412 to identify pairs having at least a threshold number of entries in the database in combination with an associated odds of the first drug developing the adverse drug reaction above a pre-defined level. This module can calculate the odds ratio and determine whether a given OR is greater than 1 using the p-value based on the Chi-Square test. The filtering module also includes a known side effects comparison module 414 to filter out pairs of drugs and ADRs that are not mentioned in one or more databases of known drug side effects. The filtering module also includes a second drug identification module 416 to identify each second drug that has been co-prescribed with the first drug for at least a threshold number of co-prescriptions.

The resulting list or set of drug combinations and targeted adverse drug reactions is communicated by the processing unit to a propensity score module 418 that calculates for each individual drug in each candidate drug combination a propensity score that is the conditional probability of being exposed to a given drug, given a set of baseline characteristics. The processing unit then using an associations module 420 to determine associations for each candidate drug combination and targeted adverse drug reaction. The associations module 420 determines how the chance developing the target ADR of interest is altered by adding the second medication, i.e., Drug B, in combination with the first medication, i.e., Drug A. This determination of the altering of the chance of developing the target ADR of interest given the addition of the second medication is determined using two separate predicted scores. The first predicted score is the predicted beneficial score for taking Drug B, i.e., given that the patient is prescribed with Drug A, whether adding Drug B will modify the chance of developing the ADR of interest. The second predicted score is the predicted interaction score, i.e., given that the patient is prescribed both Drug A and Drug B, whether Drug B will interact with Drug A to alter the chance of developing the ADR of interest. Having determined potential second drugs for each first drug and targeted adverse drug reaction, these results can be stored in the memory and communicated to a user through a communications module 422 in the computing system. Suitable outputs include displaying rank lists of second drugs and identifications of drug combinations with associated clinical benefits.

As will be appreciated by one skilled in the art, aspects of the present invention may be embodied as a system, method or computer program product. Accordingly, aspects of the present invention may take the form of an entirely hardware embodiment or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to apparatus (systems) and computer program products according to embodiments of the invention. It will be understood that each description and illustration can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the block diagram block or blocks.

The schematic illustrations and block diagrams in the Figures illustrate the architecture, functionality, and operation of possible implementations of systems, methods and computer program products according to various embodiments of the present invention. In this regard, each block in the block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams, and combinations of blocks in the block diagrams, can be implemented by special purpose hardware-based systems that perform the specified functions or acts, or combinations of special purpose hardware and computer instructions.

Methods and systems in accordance with exemplary embodiments of the present invention can take the form of an entirely hardware embodiment, an entirely software embodiment or an embodiment containing both hardware and software elements. In a preferred embodiment, the invention is implemented in software, which includes but is not limited to firmware, resident software and microcode. In addition, exemplary methods and systems can take the form of a computer program product accessible from a computer-usable or computer-readable medium providing program code for use by or in connection with a computer, logical processing unit or any instruction execution system. For the purposes of this description, a computer-usable or computer-readable medium can be any apparatus that can contain, store, communicate, propagate, or transport the program for use by or in connection with the instruction execution system, apparatus, or device. Suitable computer-usable or computer readable mediums include, but are not limited to, electronic, magnetic, optical, electromagnetic, infrared, or semiconductor systems (or apparatuses or devices) or propagation mediums. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Suitable data processing systems for storing and/or executing program code include, but are not limited to, at least one processor coupled directly or indirectly to memory elements through a system bus. The memory elements include local memory employed during actual execution of the program code, bulk storage, and cache memories, which provide temporary storage of at least some program code in order to reduce the number of times code must be retrieved from bulk storage during execution. Input/output or I/O devices, including but not limited to keyboards, displays and pointing devices, can be coupled to the system either directly or through intervening I/O controllers. Exemplary embodiments of the methods and systems in accordance with the present invention also include network adapters coupled to the system to enable the data processing system to become coupled to other data processing systems or remote printers or storage devices through intervening private or public networks. Suitable currently available types of network adapters include, but are not limited to, modems, cable modems, DSL modems, Ethernet cards and combinations thereof.

In one embodiment, the present invention is directed to a machine-readable or computer-readable medium containing a machine-executable or computer-executable code that when read by a machine or computer causes the machine or computer to perform a method for predicting beneficial drug combinations from spontaneous reporting systems in accordance with exemplary embodiments of the present invention and to the computer-executable code itself. The machine-readable or computer-readable code can be any type of code or language capable of being read and executed by the machine or computer and can be expressed in any suitable language or syntax known and available in the art including machine languages, assembler languages, higher level languages, object oriented languages and scripting languages. The computer-executable code can be stored on any suitable storage medium or database, including databases disposed within, in communication with and accessible by computer networks utilized by systems in accordance with the present invention and can be executed on any suitable hardware platform as are known and available in the art including the control systems used to control the presentations of the present invention.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A method for generating beneficial drug combinations that mitigate adverse drug reactions, the method comprising:
   identifying a candidate set of drug combinations and target adverse drug reaction triples, each drug reaction triple comprising a first drug associated with increasing a rate of occurrence of a given target adverse drug reaction and a second drug capable of reducing the rate of occurrence of the given target adverse drug reaction induced by the first drug, wherein identifying the candidate set of drug combinations and adverse drug reaction triples comprises:
      identifying an initial set of first drug and adverse drug reaction pairs having at least a threshold number of entries in a database of adverse drug events;
      generating a filtered set of first drug and adverse drug reaction pairs by identifying first drug and adverse drug reactions pairs in the initial set of first drug and adverse drug reaction pairs having an associated odds ratio of developing the adverse drug reaction from the first drug over a background level of developing the adverse reaction that is greater than one by a statistically significant amount;
      removing first drug and adverse drug reaction pairs from the filtered set that are not mentioned in at least one database of known drug side effects; and
      selecting for each remaining first drug and adverse drug reaction pair in the filtered set at least one second drug to generate the candidate set of drug combinations and adverse drug reaction triples, wherein selecting for each remaining first drug and adverse drug reaction pair in the filtered set at least one second drug comprises selecting second drugs for each remaining first drug and target adverse drug reaction pair in the filtered set such that each identified second drug has been co-prescribed with the first drug at least a threshold number of times according to case reports; and
   co-prescribing to a patient a given first drug and a given second drug from one of the drug reaction triples in the candidate set of drug combinations and target adverse drug reaction triples.

2. The method of claim 1, wherein the threshold number of entries comprises 200 entries.

3. The method of claim 1, wherein generating the filtered set comprises using a Chisquare test to determine if the odds ratio of developing a given adverse drug reaction as a result of a given first drug over a background level of developing the given adverse reaction that is significantly greater than one by a statistically significant amount.

4. The method of claim 3, wherein: using the Chi-square test comprises calculating a p-value for the odds ratio of each given first drug and adverse drug reaction pair; and generating the filtered set further comprises selecting each given first drug and adverse drug reaction pair where the p-value is less than 0.05.

5. The method of claim 3, wherein generating the filtered set further comprises using empirical probabilities to calculate odds ratios.

6. The method of claim 1, wherein the threshold number of times comprises 500.

7. The method of claim 1, selecting for each remaining first drug and adverse drug reaction pair in the filtered set at least one second drug comprises selecting for each remaining first drug and adverse drug reaction pair in the filtered set a plurality of second drugs to generate the a plurality of drug combinations and adverse drug reaction triples for each first drug and adverse drug reaction pair.

8. The method of claim 7, wherein the method further comprises outputting a ranked list of second drugs for each first drug and adverse drug reaction pair, the second drugs ranked according to an ability to reduce first drug induced adverse drug effects.

9. A computer-readable storage medium containing a computer-readable code that when read by a computer causes the computer to perform a method for generating beneficial drug combinations that mitigate adverse drug reactions, the method comprising:
   identifying a candidate set of drug combinations and target adverse drug reaction triples, each drug reaction triple comprising a first drug associated with increasing a rate of occurrence of a given target adverse drug reaction and a second drug capable of reducing the rate of occurrence of the given target adverse drug reaction induced by the first drug, wherein identifying the candidate set of drug combinations and adverse drug reaction triples comprises:
      identifying an initial set of first drug and adverse drug reaction pairs having at least a threshold number of entries in a database of adverse drug events;
      generating a filtered set of first drug and adverse drug reaction pairs by identifying first drug and adverse drug reactions pairs in the initial set of first drug and adverse drug reaction pairs having an associated odds ratio of developing the adverse drug reaction from the first drug over a background level of developing the adverse reaction that is greater than one by a statistically significant amount;
      removing first drug and adverse drug reaction pairs from the filtered set that are not mentioned in at least one database of known drug side effects; and
      selecting for each remaining first drug and adverse drug reaction pair in the filtered set at least one second drug to generate the candidate set of drug combinations and adverse drug reaction triples, wherein selecting for each remaining first drug and adverse drug reaction pair in the filtered set at least one second drug comprises selecting second drugs for each remaining first drug and target adverse drug reaction pair in the filtered set such that each identified second drug has been co-prescribed with the first drug at least a threshold number of times according to case reports; and
   co-prescribing to a patient a given first drug and a given second drug from one of the drug reaction triples in the candidate set of drug combinations and target adverse drug reaction triples.

10. The computer-readable medium of claim 9, wherein the threshold number of entries comprises 200 entries.

11. The computer-readable medium of claim 9, wherein generating the filtered set comprises using a Chi-square test to determine if the odds ratio of developing a given adverse drug reaction as a result of a given first drug over a background level of developing the given adverse reaction that is significantly greater than one by a statistically significant amount.

12. The computer-readable medium of claim 11, wherein:
   using the Chi-square test comprises calculating a p-value for the odds ratio of each given first drug and adverse drug reaction pair; and
   generating the filtered set further comprises selecting each given first drug and adverse drug reaction pair where the p-value is less than 0.05.

13. The computer-readable medium of claim 12, wherein generating the filtered set further comprises using empirical probabilities to calculate odds ratios.

14. The computer-readable medium of claim 9, wherein the threshold number of times comprises 500.

15. The computer-readable medium of claim 9, selecting for each remaining first drug and adverse drug reaction pair in the filtered set at least one second drug comprises selecting for each remaining first drug and adverse drug reaction pair in the filtered set a plurality of second drugs to generate the a plurality of drug combinations and adverse drug reaction triples for each first drug and adverse drug reaction pair.

16. The computer-readable medium of claim 15, wherein the method further comprises outputting a ranked list of second drugs for each first drug and adverse drug reaction pair, the second drugs ranked according to an ability to reduce first drug induced adverse drug effects.

17. A computing system for generating beneficial drug combinations, the computing systems comprising:
one or more computer processors, one or more computer-readable storage media, and program instructions stored on one or more of the computer-readable storage media for execution by at least one of the one or more processors, the program instructions including a method, the method comprising:
identifying a candidate set of drug combinations and target adverse drug reaction triples, each drug reaction triple comprising a first drug associated with increasing a rate of occurrence of a given target adverse drug reaction and a second drug capable of reducing the rate of occurrence of the given target adverse drug reaction induced by the first drug, wherein the selection modules comprises:
identifying an initial set of first drug and adverse drug reaction pairs having at least a threshold number of entries in the database;
generating a filtered set of first drug and adverse drug reaction pairs by identifying first drug and adverse drug reactions pairs in the initial set of first drug and adverse drug reaction pairs having an associated odds ratio of developing the adverse drug reaction from the first drug over a background level of developing the adverse reaction that is greater than one by a statistically significant amount; and a known side effects comparison module to remove first drug and adverse drug reaction pairs from the filtered set that are not mentioned in at least one database of known drug side effects;
selecting for each remaining first drug and adverse drug reaction pair in the filtered set at least one second drug to generate the candidate set of drug combinations and adverse drug reaction triples, wherein selecting for each remaining first drug and adverse drug reaction pair in the filtered set at least one second drug comprises selecting second drugs for each remaining first drug and target adverse drug reaction pair in the filtered set such that each identified second drug has been co-prescribed with the first drug at least a threshold number of times according to case reports; and
co-prescribing to a patient a given first drug and a given second drug from one of the drug reaction triples in the candidate set of drug combinations and target adverse drug reaction triples.

18. The computing system of claim 17, wherein the generating the filtered set of first drug and adverse drug reaction pairs uses a Chi-square test to determine if the odds ratio of developing a given adverse drug reaction as a result of a given first drug over a background level of developing the given adverse reaction that is significantly greater than one by a statistically significant amount, the Chi-square test comprising calculating a p-value for the odds ratio of each given first drug and adverse drug reaction pair and generating the filtered set further comprises selecting each given first drug and adverse drug reaction pair where the p-value is less than 0.05.

* * * * *